United States Patent
Rey

(10) Patent No.: US 12,187,490 B2
(45) Date of Patent: Jan. 7, 2025

(54) DELIVERY TRAY AND PACKAGING SYSTEM FOR MEDICAL ITEMS

(71) Applicant: A. Raymond et cie, Grenoble (FR)

(72) Inventor: Gaëtan Rey, Voiron (FR)

(73) Assignee: A. Raymond et Cie, Grenoble (FR)

( * ) Notice: Subject to any disclaimer, the term of this patent is extended or adjusted under 35 U.S.C. 154(b) by 0 days.

(21) Appl. No.: 18/514,841

(22) Filed: Nov. 20, 2023

(65) Prior Publication Data
US 2024/0083627 A1 Mar. 14, 2024

Related U.S. Application Data

(62) Division of application No. 17/461,815, filed on Aug. 30, 2021, now abandoned.

(30) Foreign Application Priority Data

Sep. 11, 2020 (FR) ..................................... 2009215

(51) Int. Cl.
*B65D 21/02* (2006.01)
*A61B 50/33* (2016.01)
(Continued)

(52) U.S. Cl.
CPC .......... *B65D 21/0223* (2013.01); *A61B 50/33* (2016.02); *B65D 1/36* (2013.01);
(Continued)

(58) Field of Classification Search
CPC ........ B65D 85/30; B65D 85/20; B65D 85/14; B65D 85/08; B65D 2581/05;
(Continued)

(56) References Cited

U.S. PATENT DOCUMENTS 2,646,166 A * 7/1953 Paffen .................... B65D 71/70
206/499
3,802,592 A 4/1974 Wheaton
(Continued)

FOREIGN PATENT DOCUMENTS

CA 2215561 A1 3/1998
CN 103796926 A 5/2014
(Continued)

OTHER PUBLICATIONS

European Extended Search Report and Opinion for European Application No. 21196261.8, dated Feb. 2, 2022, 11 pages.
(Continued)

*Primary Examiner* — Robert Poon
(74) *Attorney, Agent, or Firm* — TraskBritt

(57) ABSTRACT

A delivery tray for medical items includes a plurality of receiving spaces each intended to receive a single medical item. The lower face of the tray has a plurality of caps, the caps being arranged and sized such that when the tray is stacked on a second identical tray, the caps of the tray are able to close the receiving spaces of the second tray. A packaging system comprises a vessel having an opening, a bottom and a peripheral wall. The system also includes a stack formed by a plurality of trays, and a porous lid that is sealed on the upper edge of the peripheral wall of the vessel (10) to close it. The disclosure also relates to a packaging method, in particular, comprising a vacuumization step.

15 Claims, 4 Drawing Sheets

(51) Int. Cl.
*B65D 1/36* (2006.01)
*B65D 81/07* (2006.01)
*B65D 81/20* (2006.01)

(52) U.S. Cl.
CPC ......... *B65D 81/07* (2013.01); *B65D 81/2023* (2013.01); *B65D 2581/05* (2013.01)

(58) Field of Classification Search
CPC ............ B65D 21/0209; B65D 21/0201; B65D 21/02; B65D 21/00; B65D 21/0223; A61B 50/33; A61J 1/16
USPC .................... 206/499, 443, 563, 562, 504
See application file for complete search history.

(56) References Cited

U.S. PATENT DOCUMENTS

| | | | |
|---|---|---|---|
| 4,349,109 A * | 9/1982 | Scordato | B01L 9/543 |
| | | | 422/933 |
| 5,418,692 A | 5/1995 | Nemoto | |
| 5,441,702 A * | 8/1995 | Lemieux | B65D 71/70 |
| | | | 422/933 |
| 5,481,438 A | 1/1996 | Nemoto | |
| 5,948,362 A * | 9/1999 | Steinbrenner | B01L 9/543 |
| | | | 422/526 |
| 6,007,779 A | 12/1999 | Lemieux et al. | |
| 6,019,225 A | 2/2000 | Kalmakis et al. | |
| 6,475,432 B2 | 11/2002 | Balmer | |
| 6,719,141 B2 | 4/2004 | Heinz et al. | |
| 9,586,722 B2 | 3/2017 | Josef et al. | |
| 10,064,787 B2 | 9/2018 | Deutschle et al. | |
| 2001/0052476 A1 | 12/2001 | Heinz et al. | |
| 2002/0114737 A1 | 8/2002 | Madril et al. | |
| 2016/0249995 A1 * | 9/2016 | Ritchey | A61B 50/33 |
| | | | 53/425 |
| 2017/0136175 A1 | 5/2017 | Josef et al. | |
| 2017/0186636 A1 | 6/2017 | Lo | |
| 2018/0014520 A1 * | 1/2018 | Langley | B65D 21/0201 |
| 2021/0106749 A1 * | 4/2021 | Peruzzo | A61M 5/3135 |

FOREIGN PATENT DOCUMENTS

| | | |
|---|---|---|
| EP | 0285496 A1 | 10/1988 |
| EP | 0347206 A1 | 12/1989 |
| EP | 0521705 A1 | 1/1993 |
| EP | 0610100 A1 | 8/1994 |
| EP | 2753550 A1 | 7/2014 |
| EP | 2464580 B1 | 9/2016 |
| EP | 2464577 B1 | 2/2018 |
| FR | 1569978 A | 6/1969 |
| FR | 2679878 A1 | 2/1993 |
| GB | 2257121 A | 1/1993 |
| GB | 2537637 A | 10/2016 |
| JP | 05-294376 A | 11/1993 |
| WO | 01/17682 A1 | 3/2001 |
| WO | 2009/126945 A2 | 10/2009 |
| WO | 2017/136667 A1 | 8/2017 |
| WO | 2017/220876 A1 | 12/2017 |

OTHER PUBLICATIONS

Chinese Office Action for Application No. 202111062421.3 dated Jul. 29, 2024, 16 pages with English translation.

* cited by examiner

DELIVERY TRAY AND PACKAGING SYSTEM FOR MEDICAL ITEMS

CROSS-REFERENCE TO RELATED APPLICATIONS

This application is a divisional of U.S. patent application Ser. No. 17/461,815, filed Aug. 30, 2021, which pursuant to 35 U.S.C. § 119(a) claims the benefit of the filing date of French Patent Application Serial No. 2009215, filed Sep. 11, 2020, for "DELIVERY TRAY AND PACKAGING SYSTEM FOR MEDICAL ITEMS," the disclosure of each of which is hereby incorporated herein in its entirety by this reference.

TECHNICAL FIELD

The present disclosure relates to a tray and a packaging system for packaging, delivering and dispensing medical items. It also relates to a method of packaging medical items. The present disclosure relates more specifically to the packaging, with a view to their distribution, of stoppers that are intended to close medical vials.

BACKGROUND

Stoppers of this kind are generally delivered in bulk and poured into a vibrating bowl feeder, or simply placed in a tray, in order to then be placed, by hand or automatically by a machine, one by one on a vial in order to close it.

These delivery solutions are not adequate if the stoppers are intended to close vials intended for medical use. In this case, the stoppers and the vials must be free from any contamination, in particular, particulate contamination. However, if no particular precaution is taken, the contact and friction between the stoppers themselves or between the stoppers and the surfaces of the tray or vibrating bowl feeder are liable to generate particles that may then be found on the stoppers, and subsequently in the vials. This can have very serious consequences if the vial is used to contain a medical solution intended to be withdrawn by a syringe, since the particles may then be found in the syringe and then injected into the body of a patient.

It is therefore important to have a solution for packaging and delivering vial stoppers, and more generally medical items or packaging items, which makes it possible to limit the generation of particles.

Documents EP2753550 and U.S. Ser. No. 10/064,787 disclose trays and packaging systems that make it possible to individually store different types of medical items (syringes, vials). These medical items cannot contact each other, and thus the generation of particles is reduced. EP2753550 seeks, more specifically, to reduce the contact surface area between the medical items and the surface of a tray in order to reduce the friction zones.

BRIEF SUMMARY

An aim of the present disclosure is to provide a tray, a packaging system and a packaging method that differ from and improve on the prior art.

In order to achieve this aim, the object of the present disclosure provides a delivery tray for medical items, the tray comprising a lower face and an upper face, the upper face having a plurality of receiving spaces each intended to receive a single medical item.

According to the present disclosure, the lower face of the tray has a plurality of caps, the caps being arranged and dimensioned so that, when the tray is stacked on a second identical tray, the caps of the tray are able to close receiving spaces of the second tray.

According to other advantageous and non-limiting features of the present disclosure, taken alone or in any technically feasible combination:
- each receiving space is delimited laterally by a partition perpendicular to the upper face of the tray;
- each cap is delimited laterally by a wall perpendicular to the lower face of the tray;
- the caps of the tray are arranged, respectively, in line with the receiving spaces of the tray, referred to as first tray, and are dimensioned, respectively, to close the receiving spaces of a second identical tray and underlying the first tray, by interlocking or by abutment of the partitions of the receiving spaces of the second tray and the facing walls of the caps of the first tray;
- the receiving spaces each have an inner surface, the inner surface of the receiving spaces being provided with at least one lateral support element to support and limit the lateral movements of the medical item in the receiving space;
- each receiving space has a solid bottom, formed by the upper face of the tray, and each cap has a solid bottom, formed by the lower face of the tray;
- the caps are each provided with a vertical support element to support and limit the vertical movement of a medical item arranged in the receiving space of the second tray on which the tray has been stacked;
- each receiving space has a perforated bottom, and each cap has a perforated bottom, due to the presence of an orifice in the tray, centered on the bottom of each receiving space, the orifice associated with a receiving space having dimensions smaller than the dimensions of a medical item that is intended to occupy the receiving space;
- an upper part of the receiving spaces is deformable.

According to another aspect, the object of the present disclosure proposes a packaging system for medical items comprising:
- a vessel having an opening, a bottom and a peripheral wall;
- a stack formed by a plurality of trays as described above, the stack being placed in the vessel; and
- a porous lid that is sealed on an upper edge of the peripheral wall of the vessel to close it.

According to other advantageous and non-limiting features of the present disclosure, taken alone or in any technically feasible combination:
- the packaging system further comprises a cover arranged on the stack of trays to close the receiving spaces of a top tray of the stack;
- the cover is a rigid plate provided on a lower face with a plurality of caps capable of closing the receiving spaces of the top tray of the stack;
- the cover comprises a plurality of strips provided with caps capable of closing the receiving spaces of the top tray of the stack;
- the strips and the caps are made of a flexible material;
- each strip comprises bending regions formed between each cap;
- the receiving spaces of a top tray of the stack are closed by unitary stoppers;
- the bottom of the vessel is provided with bosses configured to fit into the caps of a bottom tray of the stack;

the vessel is placed, under vacuum, in at least one impermeable bag.

According to yet another aspect, the object of the present disclosure provides a method of packaging medical items comprising the following steps:

providing a vessel having an opening, a bottom and a peripheral wall;

arranging a bottom tray as described above at the bottom of the vessel;

arranging at least one additional tray as described above to form a stack of trays in the vessel, the caps of the additional tray closing the receiving spaces of a directly underlying tray;

sealing a porous lid on an upper edge of the peripheral wall of the vessel;

placing the vessel in at least one impermeable bag, and placing the bag under vacuum.

According to other advantageous and non-limiting features of the present disclosure, taken alone or in any technically feasible combination:

the lid is secured to the vessel by welding the lid to the upper edge of the peripheral wall of the vessel;

the packaging method comprises a step aimed at arranging a cover on a top tray of the stack;

the lid is also sealed to the cover.

BRIEF DESCRIPTION OF THE DRAWINGS

Other features and advantages of the present disclosure will become apparent from the following detailed description of the present disclosure, which is provided with reference to the accompanying drawings, in which.

DETAILED DESCRIPTION

General Description of the Packaging System

Figure 1:
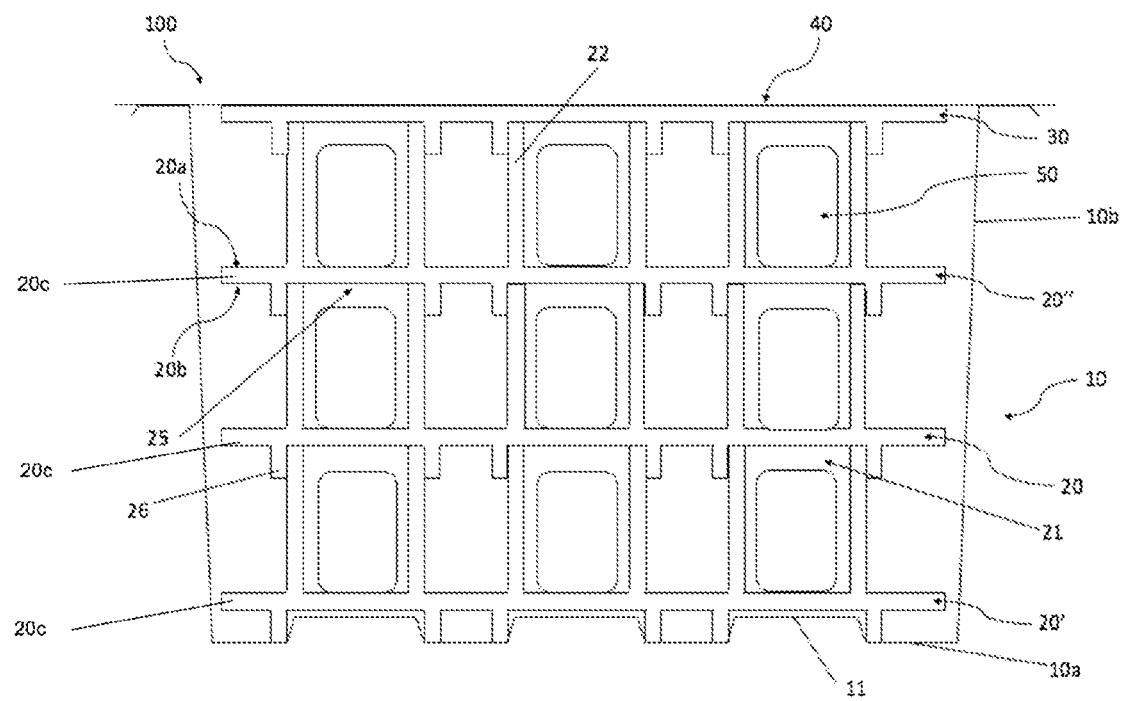
FIG. 1 shows a sectional view of packaging according to the present disclosure.

As shown in FIG. 1, a packaging system 100 according to the present disclosure comprises a vessel 10, a stack formed by a plurality of identical delivery trays 20, each provided with receiving spaces 21, stacked on top of one another parallel to the bottom 10a of the vessel 10, as well as a porous lid 40 placed on the opening of the vessel 10 to close it. The packaging system 100 can also comprise a cover 30 arranged on the top tray 20" of the stack. The vessel 10 containing the trays 20, and closed by the porous lid 40, is intended to be placed in at least one airtight bag (and generally two of these bags) in which the air has been evacuated in order to place the entire assembly under vacuum.

For the sake of clarity, it should be noted that, in the remainder of this description, the term "top tray 20'"" refers to the tray 20 of the stack located furthest from the bottom 10a of the vessel 10, and the term "bottom tray 20'" refers to the tray located closest to the bottom 10a.

Each of the trays 20 accommodates a plurality of medical items 50 stored individually in one of the receiving spaces 21 of the tray 20 without any contact being possible between them. The term "medical items 50" denotes any type of item for medical use that must remain sterile and/or clean and free from any particulate contamination. In the examples described and shown, these are stoppers intended to close vials, but they could just as easily be any other type of medical item, such as syringes or vials. The shape and volume of the receiving spaces 21 will of course be adapted such that they can accommodate the medical item 50 in question. As will become apparent in the remainder of this description, stacking the trays 20 in the vessel 10 allows the receiving spaces 21 to be closed and allows the medical items 50 placed therein to be isolated in order to limit the risk of particulate contamination.

It should be noted in this respect that medical items 50 cannot be placed in the top tray 20" of the stack. In this case, this top tray 20" serves the sole purpose of closing the receiving spaces of the tray of the stack that is directly below it. As an alternative to this possibility, and as has already been mentioned, provision can be made to arrange a cover 30 on the top tray 20" of the stack in order to close the receiving spaces thereof. This cover 30 can take various forms, which will be presented in a later section of this description.

Description of the Vessel

The vessel 10 is a hollow packaging element intended to receive the trays 20 in which the medical items 50 are placed. The vessel 10 comprises an opening, a bottom 10a and a peripheral wall 10b that delimits its general shape. The peripheral wall 10b may be provided with a shoulder that allows the vessel 10 to be handled, in particular, by automatic equipment. Advantageously, the vessel 10 has a parallelepipedal shape in order to optimize the space required for storing a given number of medical items 50. The dimensions of the vessel 10 are chosen depending on the number of medical items 50 to be packaged. These dimensions may comply with a norm or a standard so as to facilitate use on an industrial scale. The vessel 10 may be formed from a plastics material, for example, polypropylene, amorphous polyethylene terephthalate or a styrenic polymer such as polystyrene.

In the illustrated example, the bottom 10a of the vessel 10 is provided with bosses 11 allowing the bottom tray 20' to be wedged and/or centered, for example, by fitting these bosses on reliefs arranged on the lower surface of the tray 20'. These reliefs can, for example, constitute caps, which will be described in detail in a later section of the present disclosure. The bottom tray 20' (as well as the entire stack of trays) is thus immobilized in the vessel 10, the friction between the tray 20' and the vessel 10 is limited, and the generation of particles is thus prevented.

The bottom 10a of the vessel 10 may optionally comprise altitude adjustment pads (not shown) on which the bottom tray 20' will rest. These pads make it possible to adjust the height of the stacks of trays 20 so that the top tray 20" (or the cover 30, if present) is always flush with the level of the opening of the vessel 10 and of the sealing lid 40, regardless of the unit height of the trays 20; in fact, this unit height can vary depending on the size of the medical items 50.

Description of the Delivery Trays

Figure 2:
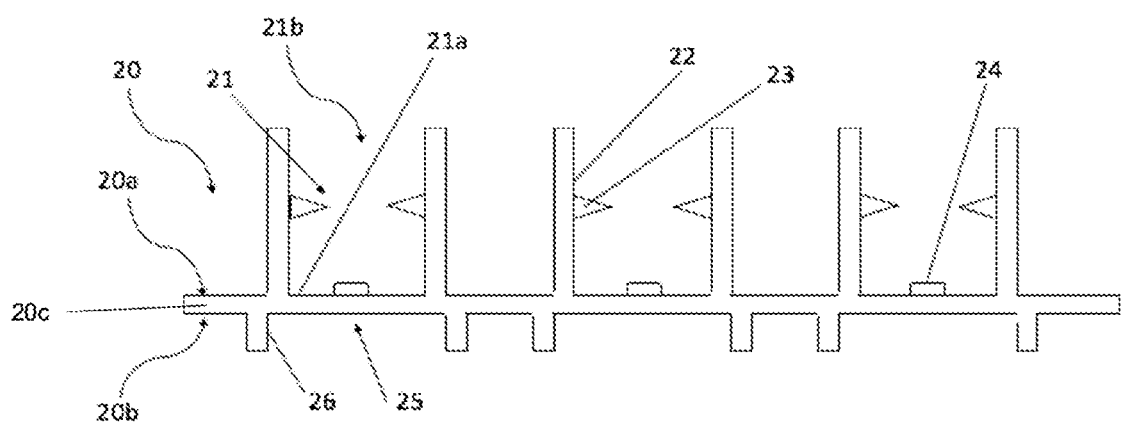
FIG. 2 shows a delivery tray according to the present disclosure.

The stack of trays 20 of FIG. 1 comprises a plurality of trays, all identical to each other, and an example of which in accordance with the present disclosure is shown in FIG. 2. Each tray 20 comprises an upper face 20a and a lower face 20b.

The upper face 20a is provided with a plurality of receiving spaces 21 each intended to receive a single medical item 50 in order to prevent any contact between two of the items 50. The receiving spaces 21 are typically arranged in rows on the upper face of the tray 20. A tray receiving space 21 has a bottom 21a, formed from the upper face 20a of the tray 20, and an opening 21b for inserting the item 50. Each receiving space 21 is delimited laterally by a partition 22, perpendicular to the upper face 20a of the tray 20, which defines its shape. This can be any shape, for example, circular, hexagonal or rectangular, adjusted to the shape and/or to the size of the medical items 50 that the receiving space 21 is intended to accommodate. The partition 22 is solid, so as to laterally isolate each of the medical items 50 when they are arranged in the receiving spaces 21.

The inner surface of the partition 22, that is to say, the surface oriented toward the inside of the receiving space 21, may be provided with at least one flexible lateral support element 23, for example, a flexible lug 23. This support element 23 makes it possible to retain the medical item 50 in the receiving space 21 and to limit its lateral movements. This reduces the possibilities of friction between the medical item 50 and the partition 22 as well as the risk of particle generation. The flexible nature of the lateral support elements 23 allows this receiving space 21 to be used for different dimensions of items 50 and thus allows the differences in dimensions to be taken into account that may exist even when these items are all identical to one another.

Advantageously, the receiving spaces 21 are each provided with at least one stop 24 to prevent extensive contact between the medical item 50 and the bottom 21a of the receiving space 21. This stop 24 allows the friction surface with the bottom to be limited and reduces particle generation. The stop may be formed by fine ribs delimited on the bottom 21a of the receiving space 21, for example, three of these ribs, or by periodic supports, for example, three of these supports.

Figure 5:
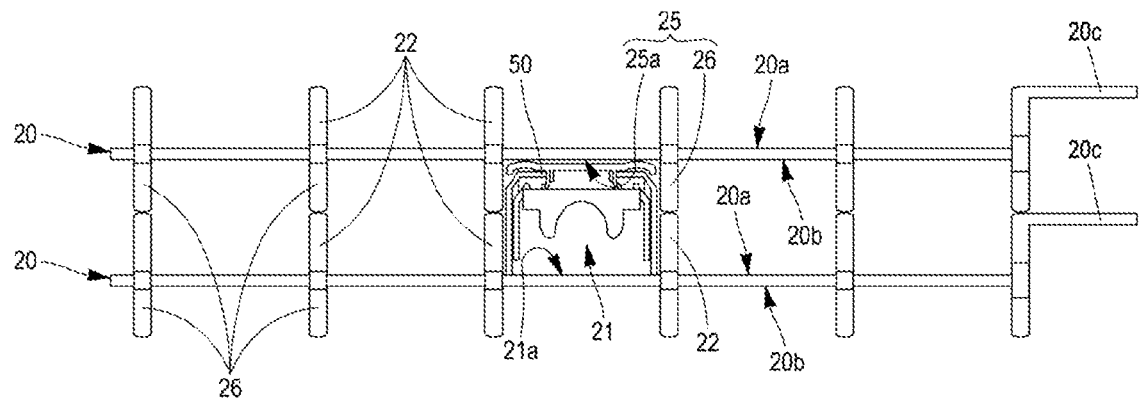
FIGS. 5, 6A and 6B show two delivery trays, stacked, according to the present disclosure; the tray receiving spaces have a solid bottom (FIG. 5) or a perforated bottom (FIGS. 6A and 6B).

The lower face 20b of the tray 20 has a plurality of caps 25, the number of caps in this plurality typically being equal to the number of receiving spaces 21 arranged on the upper face 20a of the tray 20. The caps 25 are arranged on the lower face 20b so as each to be in line with a receiving space 21. The caps 25 here are delimited by walls 26, similarly to the receiving spaces 21, so as to have dimensions complementary to those of the receiving spaces 21, so that when a first tray 20 is stacked on a second tray, identical to the first tray 20, the caps 25 of the first tray 20 are able to close, for example, by interlocking, the receiving spaces of the second tray that they overhang (FIG. 1). It is also conceivable that the walls 26 defining the caps 25 are perfectly aligned with the partitions 22 defining the receiving spaces 21 so that the receiving spaces are closed by placing, edge against edge, the walls 26 of a first tray 20 on the partitions 22 of a second tray 20, directly under it in the stack: a receiving space 21 of the second tray 20 is then closed by abutment of the partition 22 of the receiving space 21 and of the wall 26 of the cap 25, facing it, of the first tray 20 arranged on the second tray 20 (FIG. 5). The wall 26 is solid, so as to laterally isolate each of the medical items 50 when they are arranged in the receiving spaces 21 closed by the caps 25 of the upper tray 20.

Each cap 25 is also defined by a bottom 25a, formed by the lower face 20b of the associated tray 20.

As already mentioned, the caps 25 of the bottom tray 20' of the stack can also allow this tray to be assembled by fitting on the bosses 11 of the bottom 10a of the vessel 10 (FIG. 1).

Figure 3:
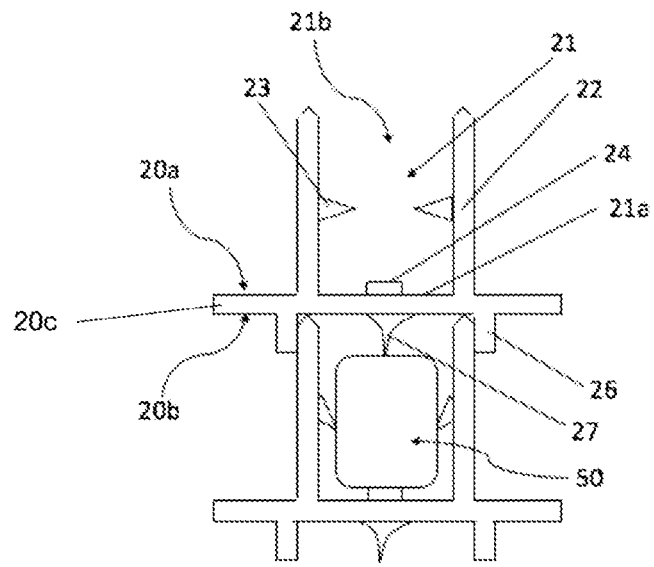
FIG. 3 shows the interactions of the stack of two trays at a receiving space according to the present disclosure.

If the receiving spaces 21 are closed by fitting, the internal dimensions of the cap 25 are advantageously greater than the external dimensions of the receiving space 21 in order to locate the possible friction region between the receiving spaces 21 and the caps 25 on the outer surface of the partitions of the receiving spaces 21, as is clearly visible in FIG. 3. In other words, the walls 26 of the caps 25 surround the partitions 22 of the receiving spaces 21 from the outside and are in contact with the outer surface of the partitions 22. This prevents particles from being generated inside the receiving spaces 21 during any friction of the walls 26 against the partitions 22. Advantageously, slight lateral play will be provided, typically between 0.1 and 1 mm, between the walls 26 defining the caps 25 and the partitions 22 defining the receiving spaces 21 in order to prevent forcing the interlocking of the trays 20 during their stacking, which could make subsequent access to the medical items retained in a tray difficult.

According to a first variant, in particular, illustrated in FIGS. 1 and 5, each receiving space 21 has a solid bottom 21a, formed by the upper face 20a of the tray 20, and each cap 25 has a solid bottom 25a, formed by the lower face 20b of the tray 20. When two trays 20 are stacked, the medical items 50 (for example, stoppers), arranged in the receiving spaces 21 of the underlying tray 20, are completely isolated from each other and protected from potential particulate contamination generated during transport of the packaging system 100 or when the latter is opened.

Figure 6A:
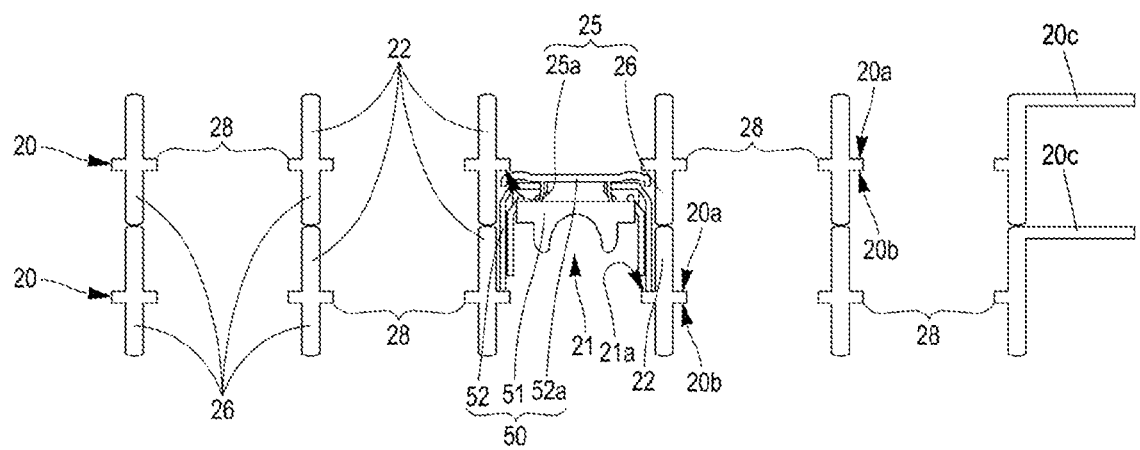
Figure 6B:
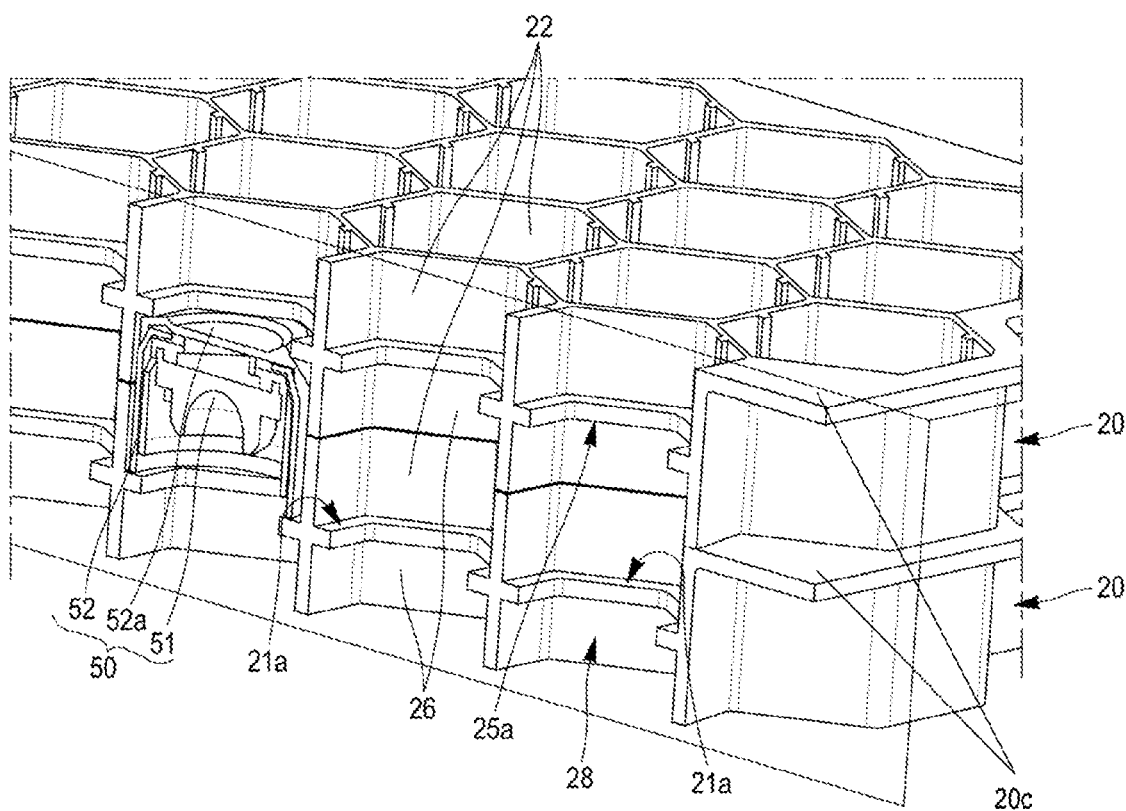

According to a second variant, illustrated in FIGS. 6A and 6B, each receiving space 21 has a perforated bottom 21a, and each cap 25 also has a perforated bottom 25a, due to the presence of an orifice 28 in the tray 20, centered on the bottom 21a of each receiving space 21. The orifice 28 associated with a receiving space 21 then has dimensions smaller than the dimensions of the medical item 50 that is intended to occupy the receiving space 21, so that the outer upper part of the medical item 50 is able to close the orifice 28. The lower part of the medical item 50 in turn is in contact with the bottom 21a of the receiving space 21.

This second variant is advantageous in that it limits the quantity of material used to manufacture a tray 20. It is particularly suitable in the case of a medical item 50 in the form of a stopper 51 provided with a locking cap 52, as shown in FIGS. 6A and 6B. The stopper 51 is usually made of an elastomeric material, having a head and a foot that is intended (in use) to be inserted into the neck of a vial. The locking cap 52 surrounds the stopper 51 and is intended (in use) to be gripped under the flange of the vial, when the foot of the stopper 51 is fully inserted into the neck: the locking cap 52 comprises retaining members able to be blocked under the collar in order to secure the stopper 51 on the vial. The locking cap 52 also comprises means ensuring the maintenance of the stopper 51 in the cap 52 during storage and transport in the packaging system 100. Non-limiting examples of medical items 50 of this type can be found in documents EP2464577 or EP2464580.

The locking cap 52 of the medical item 50 may comprise a capsule 52a forming the outer upper part of the medical item 50. As illustrated in FIGS. 6A and 6B, it is this outer upper part 52a that closes the orifice 28 and enables the medical items 50 of the same column (that is to say, directly above each other, in the stacked trays 20) to be isolated from each other.

In particular, the stopper 51 of the medical item 50, which constitutes the most sensitive part in terms of contamination, is completely isolated in the receiving space 21 of a tray 20:

by interlocking or abutment of the partition 22 of the receiving space 21 of the tray 20 with the facing wall 26 of the cap 25 of an upper tray, due to the closure of the perforated bottom 25a of the cap 25 of the upper tray by the outer upper part 52a of the locking cap 52 of the medical item 50 arranged in the receiving space 21 of the tray 20, and potentially, due to the closure of the perforated bottom 21a of the receiving space 21 by the outer upper part 52a of the locking cap 52 of a medical item 50 arranged in a tray underlying the tray 20.

In the particular case of the bottom tray 20', the closest to the bottom 10a of the vessel 10, the orifice 28 of the perforated bottom 21a of the receiving spaces 21 of the tray 20' can be closed off by providing additional caps or seals at the bottom 10a of the vessel 10, or the orifices 28 can be left open.

According to a third variant, which mixes the first and second aforementioned variants, only part (at least one) of the receiving spaces 21 of a tray 20 may have a perforated bottom 21a, the other part having a solid bottom 21a.

Returning to the general description, it is advantageously possible to provide at least some of the caps 25 with a tray 20 of vertical support elements 27 (visible in FIG. 3 in the form of a flexible tab 27), in order to maintain and limit the vertical movement of the medical items 50 arranged in the receiving spaces of the underlying tray. This reduces any friction associated with the movement of the medical item 50 within the receiving space 21. Just like for the lateral support elements 23, the flexible nature of the vertical support elements 27 allows a receiving space 21 to be used for different dimensions of items 50 and/or allows the variations in dimensions of these items to be taken into account.

Advantageously, the upper part of the receiving spaces 21, that is to say, the upper end of the partitions 22, is deformable. In the example of FIG. 3, the upper end of the partitions 22 has a pointed profile. The compressive forces exerted on the upper end of the partitions 22 during the stacking of the trays 20 lead to their deformation by crushing, which makes it possible to compensate for any defects in the flatness of the trays 20. This ensures that all the receiving spaces of the trays are properly closed, in particular, during a subsequent vacuumization step of the vessel.

The trays may be made of a plastics material, for example, polypropylene or thermoplastic elastomer or polybutylene terephthalate (PBT).

Each tray 20 advantageously comprises a peripheral gripping rim 20c, which may be located in the lateral extension of the upper 20a and lower 20b faces, as illustrated in FIGS. 1, 2 and 3. Alternatively, as can be seen in FIGS. 5, 6A and 6B, the peripheral gripping rim 20c can be located in the lateral extension of the upper end of the partitions 22 of the receiving spaces 21.

Description of the Cover

The term "cover" is used to denote any element placed in the vessel 10, on the top tray 20" of the stack, in order to close the receiving spaces thereof. This therefore avoids leaving this top tray 20" empty of any medical item 50, as has been mentioned previously.

Figure 4A:
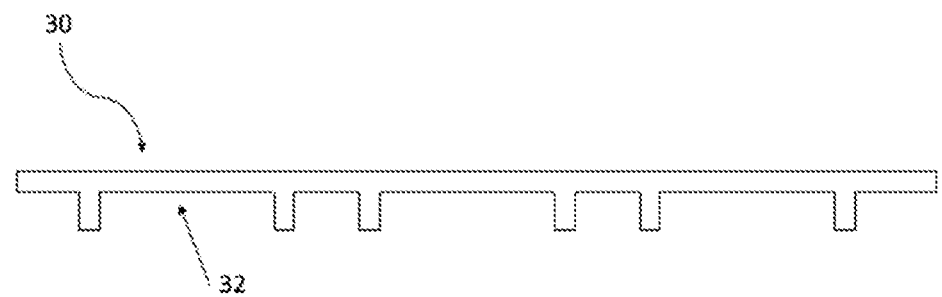
FIGS. 4A, 4B, and 4C, respectively, show a cover according to a first, second and third embodiment.

According to a first embodiment, illustrated by FIG. 4A, the cover 30 may be a rigid plate 30 provided on its lower face with a plurality of caps 32 able to close the receiving spaces 21 of the bottom tray 20', for example, by interlocking. These caps 32 are therefore identical, in their shapes, dimensions and arrangements on the lower face of the plate 30, to the caps 25 of the trays 20. The rigid plate 30 and the caps 32 may be formed from the same material as that forming the trays 20, and the plate may have similar dimensions.

In a variant of this embodiment, the plate may be composed of a plurality of individual strips 30' intended to cover and, respectively, close the rows of receiving spaces 21 of the top tray 20". These strips 30' can be secured to the porous lid 40, for example, by welding, so that removing the lid 40 (when opening the packaging system 100) naturally leads to opening the receiving spaces 21 of the top tray 20". In this embodiment in which the strips 30' are rigid, they are arranged, preferably, perpendicular to the direction of removal of the porous lid 40 in order to facilitate its removal.

Figure 4B:
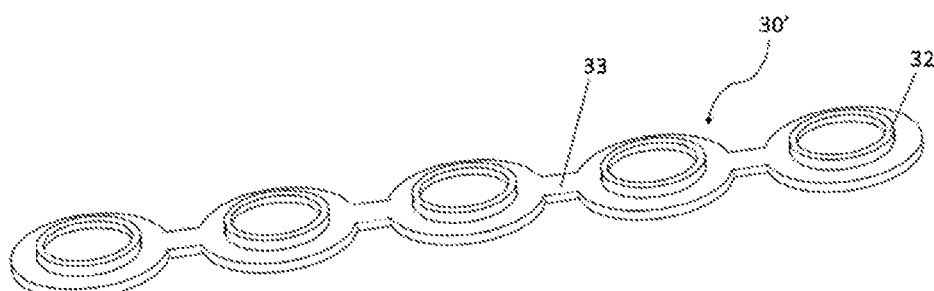

According to a second embodiment, illustrated by FIG. 4B, the cover 30 comprises a flexible plate or of a plurality of flexible strips 30', the lower face of which is provided with a cap 32 similar to those of the trays 20. Like in the first embodiment, the strips 30' are configured to close a row of receiving spaces 21 of the top tray 20" of the stack. To impart or improve the flexible nature of a strip 30', the latter can be formed by relatively narrow bending regions 33, interconnecting relatively wide support regions bearing the caps 32.

The flexible strip 30' and the caps 32 may be formed by a flexible material, for example, based on thermoplastic elastomers.

This second embodiment is very particularly advantageous when the flexible plate 30 or the strips 30' are secured to the lid 40 that closes the vessel 10. The receiving spaces 21 of the top tray 20" of the stack placed in this vessel are then opened when this lid is removed, and the medical items 50 stored in the receiving spaces 21 of the top tray 20" are immediately accessed. If the strips 30' are flexible enough, they can be arranged without any particular orientation with respect to the opening direction of the lid 40.

Figure 4C:
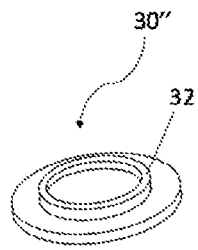

According to a third embodiment, illustrated by FIG. 4C, provision can also be made for the cover 30 to be implemented by a plurality of unitary caps 30", these caps being arranged, respectively, on the receiving spaces of the top tray 20" in order to close them. They can be soft or rigid caps.

Description of the Lid

The porous lid 40 is intended to be sealed, for example, by means of plastic welding, on the upper edges of the peripheral wall 10b of the vessel 10, once the vessel has been filled with the trays 20 carrying the medical items 50 and optionally the cover. The porous lid is intended to keep the medical items 50 clean and to prevent particles from entering the vessel 10. The air porosity of the lid 40 makes it possible to extract the air from the vessel during a subsequent vacuumization step. It may be, for example, made of TYVEK®, a material commonly used in the pharmaceutical industry.

When provision is made to place a cover 30 in the vessel on the top tray 20" of the stack, as has already been mentioned with reference to the two embodiments of this cover 30, the porous lid can also be sealed, for example, by welding, to this cover 30 simultaneously with its sealing on the upper edges of the peripheral wall 10b of the vessel 10.

To allow this, the elements of the packaging system 100 are dimensioned so that the exposed surface of the cover 30 (whichever embodiment is chosen), when the latter is placed on the top tray 20" of the stack of trays, is flush with the upper edge of the wall of the vessel 10.

Description of the Packaging Method

In order to minimize contamination by particles and in order to preserve the possible sterility of the medical items 50, the various steps described below are carried out, preferably, in a controlled environment.

A first tray 20', the bottom tray 20' of the stack, is arranged on the bottom 10a of the vessel 10 so as to align and fit the caps 25 of the lower face 21a of the first tray 20' with the bosses 11 of the bottom 10a of vessel 10 (if present). Medical items 50 are then, or were previously, placed in the receiving spaces 21 of the first tray 20'.

Then, a second tray 20 is arranged on the first tray 20'. The caps 25 arranged on the lower face of the second tray close the receiving spaces 21 of the first tray 20'. Medical items 50 are arranged in each receiving space 21 of the second tray 20 before or after this operation. This is repeated as many times as there are trays 20 to be placed in the vessel 10 and until the last tray 20" is placed, forming the top tray 20" of the stack.

In the event that no cover 30 is provided, the last tray 20" is kept empty, that is to say, without placing medical items in its receiving spaces 21.

Otherwise, a cover 30 is placed on the upper face 20a of the top tray 20" of the stack in order to close its receiving spaces 21, in which the medical items have been placed beforehand. As has already been mentioned, this cover can be formed by a plate provided with caps, which is therefore arranged integrally on the top tray 20". It may be, alternatively, a plurality of flexible or rigid strips 30' bearing caps, and placed in rows on the top tray 20" so as to close the receiving spaces 21, or else unitary caps 30" arranged on each receiving space 21. Optionally, a combination of these options can be used to close the receiving spaces 21 of the top tray 20".

The porous lid 40 is then arranged on the top tray 20" or on the cover 30, then secured to the upper edges of the wall 10b of the vessel 10, as well as possibly to the flexible plate 30 or to the strips 30' and/or unitary caps 30" when these are present.

In a following step, the vessel 10, the opening of which has been closed by the porous lid 40, is placed in at least one airtight bag (and, preferably, two bags for safety reasons), and the vacuumization is carried out in this bag before it is hermetically sealed. The vacuumization of the assembly allows the various components of the assembly 100 to be blocked vertically, and therefore allows each receiving space 21 to be closed individually. Any defects in the flatness of the trays 20 and of the cover 30 are compensated for by the deformable nature of the partitions 22 of the receiving spaces 21 and by the relative flexibility of the trays 20. The vacuumization also makes it possible to horizontally block the various components of the assembly 100 by deforming the peripheral wall 10b of the vessel 10 in order to press it against the edge of the trays 20. The vacuumization therefore makes it possible to limit the friction between the various elements of the assembly 100 and thus the generation of particles by friction by blocking the vertical and horizontal movement of the elements.

Opening the Packaging System

To open the packaging system and access the medical items packaged therein, the vessel 10 containing the stack of trays 20 is first of all taken out of the bag. The lid 40 is then removed to expose the cover 30, when the latter is present. The cover 30 is extracted from the vessel, for example, using a suction cup when the latter is in the form of a rigid plate, to expose the receiving spaces 21 of the top tray 20". When it is in the form of rigid or flexible strips sealed to the lid 40, opening this lid naturally leads to removing the caps from the receiving spaces 21, without any additional operation. The medical items 50 can then be picked up individually or row by row, manually and/or automatically by a machine. Once the top tray 20" has been emptied of its medical items 50, the latter is also removed to expose the receiving spaces 21 and the medical items 50 of the underlying tray 20. These operations are repeated until all the medical items 50 stored in the vessel 10 have been removed.

Of course, the present disclosure is not limited to the embodiments described and it is possible to add variants without departing from the scope of the invention as defined by the claims.

Although a single type of receiving space delimited by partitions has been described here, other shapes or configurations could be envisaged. The receiving spaces can, for example, be arranged in cells to optimize the space in the vessel, the inner surface of a partition of one receiving space forming the outer surface of a partition of another receiving space. The receiving spaces could equally well correspond to a recess formed in a tray or be a combination of recesses and partitions.

Finally, although here is put forward a fitting of the caps on the receiving spaces carried out from the outside to locate the possible friction region on the outer surface of the receiving spaces, it is, of course, possible to have the reverse. In this case, the external dimensions of the cap 25 are smaller than the internal dimensions of the receiving space 21 so that the fitting of the cap 25 takes place from the inside.

What is claimed is:

1. A packaging system comprising:
   a top delivery tray comprising:
   an upper face comprising a receiving space;
   a lower face comprising a cap associated with the receiving space; and
   an orifice extending through the delivery tray between the receiving space and the cap, the orifice forming a perforated bottom in the receiving space and the cap;
   a bottom delivery tray identical to the top delivery tray, the bottom delivery tray comprising:
   an upper face comprising a receiving space;
   a lower face comprising a cap associated with the receiving space; and
   an orifice extending through the delivery tray between the receiving space and the cap, the orifice forming a perforated bottom in the receiving space and the cap; and
   a single medical item stored in the receiving space of the bottom delivery tray, the single medical item comprising a stopper and a locking cap surrounding and maintaining the stopper, and the locking cap comprising a capsule forming an outer upper part of the single medical item,
   wherein the receiving space of the bottom delivery tray is configured and sized such that when the top delivery tray is stacked on the bottom delivery tray, the cap of the top delivery tray closes the receiving space of bottom delivery tray so as to completely enclose the single medical item stored in the receiving space of the bottom delivery tray, and
   wherein the orifice of the bottom delivery tray and the orifice of the top delivery tray comprise dimensions that are smaller than dimensions of the capsule of the single medical stored in the receiving space of the bottom delivery tray, so that when the top delivery tray is stacked on the bottom delivery tray, the orifice of the cap of the top delivery tray is closed by the outer upper part of the medical item.

2. The packaging system of claim 1, wherein
the receiving space of each of the top delivery tray and the bottom delivery tray is delimited laterally by a partition perpendicular to the upper face of the tray,
the cap of each of the top delivery tray and the bottom delivery tray is delimited laterally by a wall perpendicular to the lower face of the tray, and
the cap of each of the top delivery tray and the bottom delivery tray is arranged in line with the receiving space of each of the top delivery tray and the bottom delivery tray and is sized such that the cap of the top delivery tray closes the receiving space of the bottom delivery tray by interlocking or abutment of the partition of the receiving space of the bottom delivery tray and the wall of the cap of the top delivery tray.

3. The packaging system of claim 1, wherein the receiving space of each of the top delivery tray and the bottom delivery tray comprises an inner surface, the inner surface of the receiving space comprising at least one lateral support element to support and limit lateral movements of the single medical item in the receiving space.

4. The packaging system of claim 1, wherein the orifice of each of the top delivery tray and the bottom delivery tray is centered on the perforated bottom of the receiving space of each of the top delivery tray and the bottom delivery tray.

5. The packaging system of claim 1, wherein an upper part of the receiving space of each of the top delivery tray and the bottom delivery tray is deformable.

6. The packaging system of claim 1, further comprising:
a vessel having an opening, a bottom and a peripheral wall;
a stack formed by the top delivery tray and the bottom delivery tray, the stack being placed in the vessel; and
a porous lid that is sealed on an upper edge of the peripheral wall of the vessel to close it.

7. The packaging system of claim 6, further comprising a cover arranged on the stack to close the receiving space of the top delivery tray.

8. The packaging system of claim 7, wherein the cover is a rigid plate provided on a lower face with a cap configured to close the receiving space of the top delivery tray.

9. The packaging system of claim 7, wherein the cover comprises a strip comprising a cap operable to close the receiving space of the top delivery tray.

10. The packaging system of claim 9, wherein the strip comprises a flexible material.

11. The packaging system of claim 10, wherein the strip comprises bending regions.

12. The packaging system of claim 6, wherein the receiving space of the top delivery tray of the stack is closed by a unitary stopper.

13. The packaging system of claim 6, wherein the bottom of the vessel is provided with a boss configured to fit into the cap of the bottom delivery tray of the stack.

14. The packaging system of claim 6, wherein the vessel is placed under vacuum in at least one sealed bag.

15. The packaging system of claim 1, wherein a vertical dimension of the receiving space of each of the top delivery tray and the bottom delivery tray and a vertical dimension of the cap of each of the top delivery tray and the bottom delivery tray are sized such that the capsule is flush with the perforated bottom of the cap of the top delivery tray when the top delivery tray is stacked on the bottom delivery tray.

* * * * *